(12) United States Patent
Gandyra

(10) Patent No.: US 8,411,917 B2
(45) Date of Patent: Apr. 2, 2013

(54) DEVICE FOR DETERMINING THE 3D COORDINATES OF AN OBJECT, IN PARTICULAR OF A TOOTH

(75) Inventor: Michael Gandyra, Rosenheim (DE)

(73) Assignee: Steinbichler Optotechnik GmbH, Neubeuern (DE)

( * ) Notice: Subject to any disclaimer, the term of this patent is extended or adjusted under 35 U.S.C. 154(b) by 1111 days.

(21) Appl. No.: 12/228,917

(22) Filed: Aug. 18, 2008

(65) Prior Publication Data
US 2009/0087050 A1  Apr. 2, 2009

(30) Foreign Application Priority Data

Aug. 16, 2007  (DE) .................. 10 2007 038 721
Dec. 14, 2007  (DE) .................. 10 2007 060 263

(51) Int. Cl.
*G06K 9/00*  (2006.01)
*A61B 1/04*  (2006.01)

(52) U.S. Cl. .......................................... 382/128; 396/16

(58) Field of Classification Search ............... 382/128; 396/7, 14, 16–17; 356/603
See application file for complete search history.

(56) References Cited

U.S. PATENT DOCUMENTS

| 4,640,620 | A  | * | 2/1987  | Schmidt .................. 356/609 |
| 5,347,454 | A  | * | 9/1994  | Mushabac ............... 433/214 |
| 7,259,871 | B2 | * | 8/2007  | Chen ...................... 356/603 |
| 7,372,642 | B2 | * | 5/2008  | Rohaly et al. ........... 359/740 |
| 7,437,062 | B2 | * | 10/2008 | Holcomb ................. 396/7 |
| 7,688,998 | B2 | * | 3/2010  | Tuma et al. .............. 382/103 |
| 2007/0208252 | A1 | * | 9/2007  | Makower ................. 600/424 |
| 2007/0299334 | A1 | * | 12/2007 | Vilsmeier ................ 600/414 |
| 2008/0108869 | A1 | * | 5/2008  | Sanders et al. .......... 600/109 |
| 2010/0239136 | A1 | * | 9/2010  | Gandyra et al. ......... 382/128 |

* cited by examiner

*Primary Examiner* — Christopher Mahoney
(74) *Attorney, Agent, or Firm* — Dilworth & Barrese LLP.

(57) ABSTRACT

A scanner is used for scanning an object (3, 4, 5), in particular a tooth or a plurality of teeth or a dental cast. The scanner (1) comprises a projector (2) for projecting a pattern (7) onto the object (3, 4, 5) and a camera which comprises a recording optics and an image sensor (18). To improve such scanner, the recording optics comprises a first imaging optics (9) and a second imaging optics (10).

17 Claims, 2 Drawing Sheets

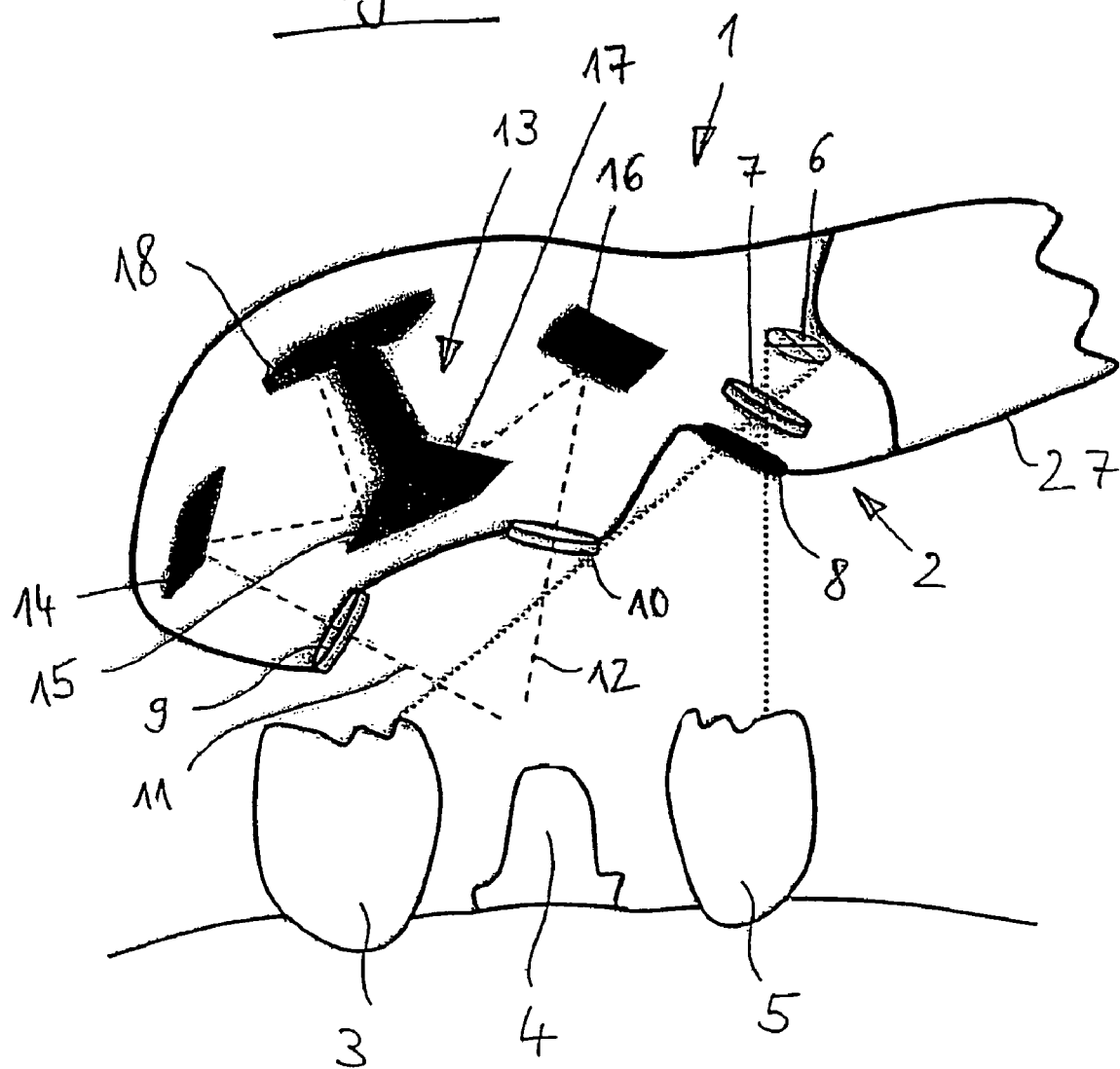

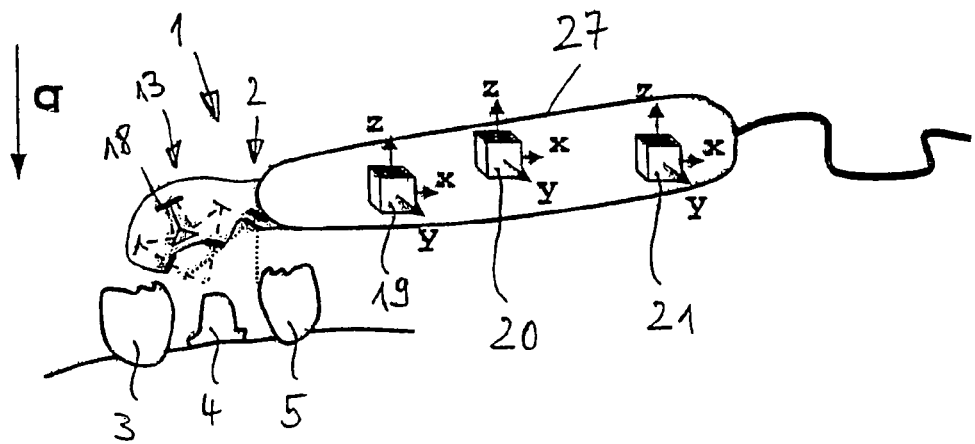
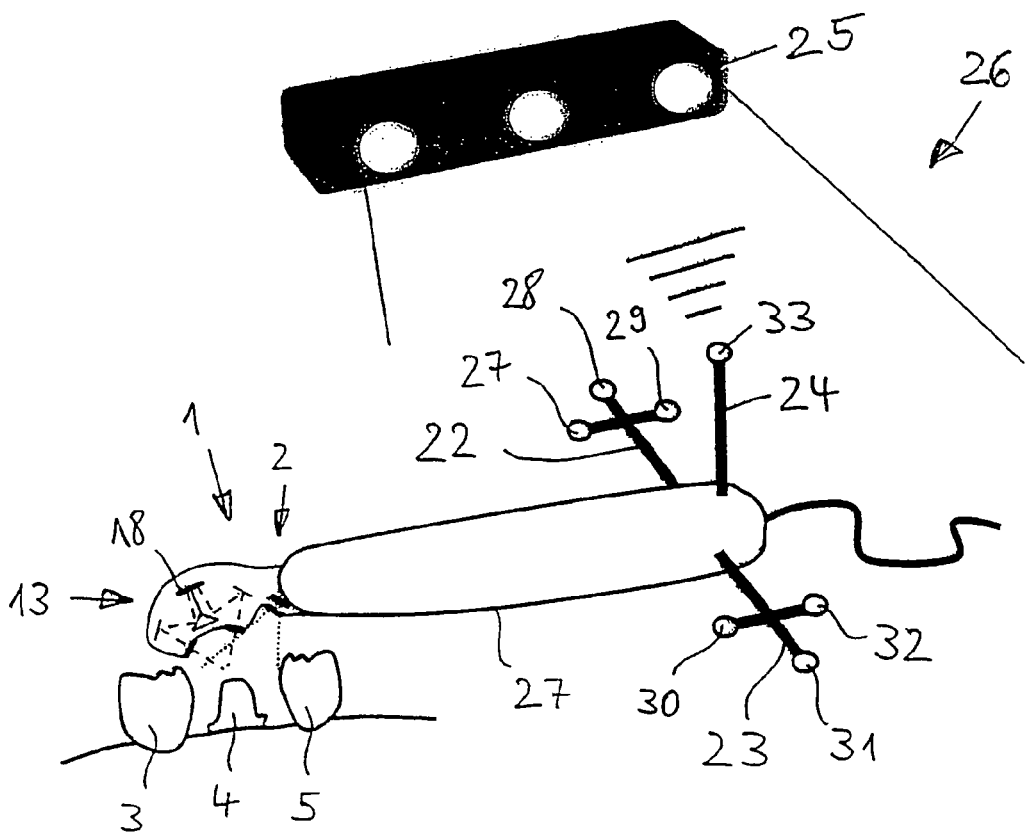

DEVICE FOR DETERMINING THE 3D COORDINATES OF AN OBJECT, IN PARTICULAR OF A TOOTH

BACKGROUND OF THE INVENTION

This invention relates to a scanner for scanning an object, in particular a tooth or a plurality of teeth or a dental cast, and a device for determining the 3D coordinates of an object, in particular of a tooth or a plurality of teeth or a dental cast.

Devices and methods for determining the 3D coordinates of an object are known already. EP 299 490 B2 describes a method for making a dental prosthesis, in which contour lines on the ground tooth and its surroundings are produced, the lines are detected with an optoelectronic means, in particular a video camera, the detected values are entered in a computer, and the three-dimensional structure of the tooth and the dental prosthesis is calculated. By means of the structure thus calculated, the dental prosthesis can be fabricated.

SUMMARY OF THE INVENTION

However, the detection of the 3D coordinates of objects located in regions which are hard to reach, i.e. in particular of teeth in the oral cavity of a patient, involves certain difficulties.

Proceeding therefrom, it is the object underlying the invention to propose an improved scanner for scanning an object, in particular a tooth, and an improved device for determining the 3D coordinates of an object, in particular of a tooth.

In accordance with the invention, this object is solved by a scanner with the features herein. The scanner is used for scanning an object, in particular one or more teeth, wherein one or more or all teeth can be prepared. The term of preparing on the one hand comprises the dental preparation, i.e., for instance grinding the stump of a tooth, and on the other hand the preparation which is necessary for scanning a tooth with an optical measurement technique, for instance spraying white spray onto the region to be scanned.

The scanner comprises a projector for projecting a pattern onto the object and a camera which comprises a recording optics and an image sensor, in particular a CCD sensor or a CMOS sensor. In accordance with the invention, the recording optics comprises a first imaging optics and a second imaging optics. In this way, a stereoscopic pair is produced by the scanner. The imaging optics can be located at a distance from each other. The optical axes of the imaging optics can be arranged at an angle with respect to each other. Preferably, they are arranged at such an angle with respect to each other that they are directed towards a corresponding region of the object or tooth. As a result, the region of the object or tooth thus is observed with two cameras.

The scanner of the invention in particular can constitute a miniaturized scanner. It is particularly useful for scanning teeth in the mouth of a patient. It is, however, also particularly useful for other applications in which the objects to be scanned are hard to reach. In particular, the scanner of the invention can be used for intra-ear scanning, for endoscopic digitization and/or in hard-to-reach cavities and/or channels of machines and/or apparatuses.

Advantageous developments are described herein.

Preferably, the recording optics comprises a beam splitter. The images from the imaging optics can be supplied to the beam splitter. The beam splitter can project these images onto the image sensor. In doing so, the images from the imaging optics can each be projected onto different regions of the image sensor.

It is possible to provide further imaging optics. In particular, two more imaging optics can be provided, so that a total of four imaging optics are present. Each image can be projected onto a separate quarter of the image sensor.

It is furthermore possible to provide further image sensors. In particular, one image sensor can be present for each imaging optics.

By taking a picture, a particular region of the object or tooth can be covered. To be able to cover the entire object or the entire tooth or several or all teeth and possibly also the surroundings thereof, a plurality of pictures can be taken sequentially. The individual shots can be combined to a total object representation.

For this purpose, the scanner is moved around the object, in order to cover several or all regions of the object. Since the scanner makes each individual shot in its coordinate system, the movement of the scanner advantageously should be detected, so as to be able to combine the individual shots as detailed and accurate as possible. This procedure is referred to as "registering" or "matching".

In accordance with an advantageous development, the scanner includes one or more sensors for detecting the location and orientation of the scanner. In this way, a tracking system can be formed for the scanner.

For detecting the location and orientation of the scanner, 6D data preferably are supplied by the sensor(s). The 6D data consist of three translational data and three rotational data. As a result, both the translation and the rotation of the scanner are detected completely. In this way, a tracking system is formed for the scanner.

In accordance with another advantageous development, the scanner includes one or more acceleration sensors. The scanner movement can be detected by the acceleration sensors, and the location of the scanner can be determined thereby. It is possible to detect the location of the scanner by the acceleration sensors.

In accordance with another advantageous development, the scanner includes one or more gyrometers. The rotations, i.e. the orientation, of the scanner can be detected by the gyrometers.

The 6D information corresponds to the six degrees of freedom, which must be defined to unambiguously define a body, namely the scanner, in space in terms of its location (position) and orientation (rotation). The 6D information of the scanner is defined by three translatory components and three rotary components.

The temporal integration of an acceleration sensor supplies a velocity. The further temporal integration thereof supplies a path component. Proceeding therefrom, three acceleration sensors can be used. Sensors which determine all three translatory components at the same time are, however, also available.

The same is true for gyrometers, which detect the rotary accelerations, whose temporal integration two times over supplies an angle of rotation. It is possible to use three gyrometers, in order to obtain the three spatial angles of rotation of the scanner. However, there are also gyrometers which supply all three spatial angles of rotation.

Furthermore, there are sensors which supply all three translations and all three rotations.

Instead or in addition, markers for a tracking system can be provided on the scanner. The markers for the tracking system can be one or more active markers. In particular, infrared markers can be used, which are triggered time-sequentially. However, the markers for the tracking system can also be one or more passive markers. In particular, the passive markers can be coded and/or non-coded, reflecting and/or non-reflecting markers. The markers can have different patterns.

The markers present on the scanner initially are surveyed. Hence, the position of the markers on the scanner is known. The markers then are tracked by a tracking camera. By means of the tracking system, the location and rotary position of the scanner can be covered in the different shots. In this way, possibilities for combining the different individual shots of the scanner are improved or created.

In a device for determining the 3D coordinates of an object, in particular of a tooth, the object underlying the invention is solved by the features of claim 12. The device comprises an inventive scanner for scanning the object or tooth and an evaluation means, in particular a computer, especially a PC including the associated software, for determining the 3D coordinates of the object from the pictures taken by the scanner.

Preferably, the device in accordance with the invention comprises a tracking system for determining the location and orientation of the scanner. The tracking system can be formed in that the scanner includes one or more sensors for detecting the location and orientation of the scanner. In particular, the tracking system can be formed in that the scanner includes acceleration sensors and/or gyrometers. It is possible that the data of the sensor(s) for detecting the location and orientation of the scanner and/or of the acceleration sensors and/or of the gyrometer(s), in particular the 6D data thereof, are calculated back onto the location and rotary position of the scanner by temporal integration. Instead or in addition, however, another tracking system can also be used, in particular an infrared tracking system.

BRIEF DESCRIPTION OF THE DRAWINGS

Embodiments of the invention will be explained in detail below with reference to the attached drawing, in which:

FIG. 1 shows a scanner for scanning a group of teeth in a schematic view,

FIG. 2 shows the scanner of FIG. 1, which additionally includes acceleration sensors, and FIG. 3 shows the scanner of FIG. 1 with infrared markers for an infrared tracking system.

DESCRIPTION OF THE PREFERRED EMBODIMENTS

FIG. 1 shows a scanner 1 which includes a projector 2 for projecting a pattern onto the teeth 3, 4, 5. The tooth 4 is ground, the adjacent teeth 3, 5 are not ground and form the surroundings of the ground tooth 4. The projector 2 comprises a light source 6, a pattern transparency 7 and a projection optics 8. The light source 6 can be a light bulb or an LED. Instead of the pattern transparency 7 a transmitted-light LCD can also be used, which can be activated for forming a pattern. The pattern can, however, also be projected by means of a DMD or LCOS method.

In the scanner 1, a first imaging optics 9 and a second imaging optics 10 furthermore are provided, which are spaced from each other and whose optical axes 11, 12 form an angle with respect to each other. The distances of the imaging optics 9, 10 and the directions of the optical axes 11, 12 are chosen such that they are directed towards a common region of the ground tooth 4.

The scanner 1 furthermore comprises a beam splitter 13. In the optical path from the imaging optics 9 to the beam splitter 13 a first mirror 14 is provided, which reflects the light which comes from the first tooth 4 and is projected by the first imaging optics 9 onto the first mirror 15 of the beam splitter 13. Correspondingly, a second mirror 16 is provided in the optical path of the second imaging optics 10, which reflects the light coming from the ground tooth 4 and projected by the second imaging optics 10 to the second mirror surface 17 of the beam splitter 13. From the mirror surfaces 15, 17 of the beam splitter 13, the light is reflected to a CCD sensor 18. The image from the first imaging optics 9 is projected onto the left half of the CCD sensor 18, the image from the second imaging optics 10 is projected onto the right half of the CCD sensor 18. The images from the imaging optics 9, 10 are supplied to the beam splitter 13, which projects the same onto different regions of the CCD sensor 18. In this way, a stereoscopic pair is produced on the CCD sensor 18, which can be evaluated by a software present on a PC. The CCD sensor 18 can constitute a divided CCD chip.

The scanner shown in FIG. 2 corresponds to the scanner shown in FIG. 1, so that the components explained above will not be described again. The scanner as shown in FIG. 2 additionally includes sensors for detecting the location and orientation of the scanner 3. These sensors are three acceleration sensors 19, 20, 21, which each supply data in x-, y- and z-direction, from which 6D data can be derived. These acceleration data can be integrated temporally, so that the position in space and the rotary position of the scanner can be determined therefrom. The acceleration sensors 19, 20 are disposed in the handle 27 of the scanner 1.

FIG. 3 shows the scanner 1 of FIG. 1 or 2 with cantilevers 22, 23, 24, at whose ends infrared markers 27, 28, 29; 30, 31, 32; 33, in particular infrared diodes, are provided, which supply data for an infrared tracking camera 25. The infrared markers 27-33 emit infrared beams, which are received by the infrared tracking camera. The tracking system 26, which consists of the markers 27-33 and the camera 25, can determine therefrom the location and orientation of the hand-guided scanner 1.

The method can be performed such that the infrared diodes 27-33 light up one after the other. This is time-sequentially detected by the tracking camera 25 (which can be a 3-line camera), from which the distance can be determined. The interconnection of the infrared markers 27-33 is unambiguously defined by its calibration. As a result, location and orientation in space can be calculated. The more markers can be evaluated, the more precisely can location and orientation be determined (some markers for instance are concealed during the measurement).

By means of the invention, a meteorological method can be performed, which is based on the evaluation of stereoscopic pairs. In the method, an object is observed with two cameras. With suitable algorithms, the same features can be found and correlated in both images. In calibrated systems, i.e. when the location and orientation of both cameras are known, a distance value and hence a 3D coordinate—in the coordinate system of the scanner—can be calculated for each object point, which can be observed in both cameras. The recording optics is equipped with a beam splitter. In this way, the scanner can be miniaturized. The object to be scanned, in particular a dental preparation or an object in a hard-to-reach region of a machine or apparatus, can be observed from two directions. The same scene is projected from two directions onto only one image sensor or CCD chip. An extension to more than two directions, in particular to four directions, is possible. All images can be projected onto one CCD chip. It is, however, also possible to use a plurality of image sensors.

To find the same features of the object in the different images, a pattern is projected onto the object. By means of the projected pattern, the associated image regions can be found in both images.

The pattern to be projected can be a stochastic or ordered pattern. It can consist of lines or cross gratings. It can be a time-constant or time-variable or time-sequential pattern. The pattern can be any graphical pattern (dots, lines, grating, etc.). The pattern can be a grey-scale pattern or a color pattern. The pattern can be projected with transmitted light, for instance as a chrome mask (transparency) or as an LED projection. The pattern can, however, also be projected by reflection, for instance as an LCOS or DLP projection.

One image recording each can produce a data recording in the form of a 3D aggregate of points. However, the same can represent only part of the entire representation of the real object. For this reason, a plurality of individual shots of the object can be made successively, and these individual shots can be combined to form one total object representation. To achieve this, the scanner can be moved around the object, in order to cover all regions of the object. Instead or in addition, the scanner can be tracked, e.g. by an externally mounted tracking system.

The present invention creates a method and a device for dynamically covering the surfaces of objects, in particular for the dynamic intraoral coverage of the surfaces of dental preparations. A pattern is projected onto the surface, which is observed from two or more directions for generating the digital 3D data and is included in a corresponding number of 2D images. There can be effected a photogrammetric evaluation of the 2D images, and the time-sequential individual 3D images calculated therewith can be combined by means of a tracking system by determining the location and orientation of the scanner in space.

The photogrammetric evaluation can be an evaluation of stereoscopic pairs, which represent the object to be surveyed from two different directions. It can, however, also be an evaluation of several images from several views, in particular an evaluation of four images from four views. The stereoscopic pair can be an individual image, which consists of two image halves which were taken from two viewing directions. Four individual shots can be combined in four "image quarters".

The tracking system can be an optical or an interferometric tracking system. It is, however, also possible to realize the tracking system by sensors for detecting the location and orientation of the scanner, which are attached to the scanner, and/or by acceleration sensors and/or gyrometers, by means of which the velocity and position of the scanner can be calculated back via the temporal integration. The acceleration sensors can supply three translational data. The gyrometers can supply three rotational data, i.e. data on the orientation of the scanner. It is particularly advantageous to provide both acceleration sensors and gyrometers, so as to obtain 6D data.

By means of the invention it is possible to determine the 3D coordinates of an object. This can be accomplished in that the 3D coordinates are calculated by correlating identical features in several, in particular two, images. By this method, associated identical image points can be found in both images of a stereoscopic pair, which were taken from different directions. By calibrating the imaging optics and by triangulation, the 3D coordinates of the object points thus can be calculated. To be able to provide an unambiguous allocation of the same features in the images, a pattern is projected. The projected pattern is used for this process referred to as feature recognition. In this method, the projector is not part of the calibration; it is independent of the stereo camera system.

It is, however, also possible to perform other methods for determining the 3D coordinates of the object. In particular, methods of the "single-image measurement technique" can be performed, i.e. methods with which the 3D coordinates of the object can be calculated from a single image recording. To be able to perform this method and to avoid a plurality of sequential image recordings of the same region, the picture taken must contain all data necessary for calculating the 3D coordinates. To ensure this, a pattern usually is projected onto the object. To be able to project this pattern, different properties of the light can be utilized. The pattern can, for instance, be a cross grating with different colors, as it is described in DE 102 12 364 A1. In this method, the projector must be calibrated together with the camera. The method can be performed such that with the image from an imaging optics and with the projected pattern the 3D coordinates are calculated and that these 3D coordinates are correlated and optimized with the coordinates calculated from an image of the other imaging optics and from the projected pattern.

The invention claimed is:

1. A scanner for scanning an object (3,4,5) with a projector (2) for projecting a pattern (7) onto the object (3,4,5) and with a camera which comprises a recording optics and an image sensor (18), wherein the recording optics comprises a first imaging optics (9) and a second imaging optics (10) and a beam splitter (13) positioned to receive light respectively projected from the first imaging optics (9) and second imaging optics (10) and then reflecting the light to the image sensor (18) and additionally comprising first and second mirrors (14, 16) each positioned to respectively reflect the light projected from the first and second imaging optics (9, 10) to the beam splitter (13).

2. The scanner according to claim 1, wherein the scanner (1) includes one or more sensors for detecting the location and orientation of the scanner (1).

3. The scanner according to claim 2, wherein the one or more sensors supply 6D data.

4. The scanner according to claim 2, comprising three said acceleration sensors (19, 20, 21) each arranged for respectively supplying data in x-, y- and z-directions to determine both spatial and rotary position of the scanner (1).

5. The scanner according to claim 4, additionally comprising a handle (27) on which the acceleration sensors (19, 20, 21) are mounted.

6. The scanner according to claim 1, wherein the scanner (1) includes one or more acceleration sensors (19, 20, 21).

7. The scanner according to claim 1, wherein the scanner (1) includes one or more gyrometers.

8. The scanner according to claim 1, wherein markers (27, 28, 29; 30, 31, 32; 33) for a tracking system (26) are provided on the scanner (1).

9. The scanner according to claim 8, wherein the markers are active markers.

10. The scanner according to claim 8, wherein the markers are passive markers.

11. The scanner according to claim 8, additionally comprising cantilevers (22, 23, 24) on which the markers (27, 28, 29; 30, 31, 32; 33) are mounted.

12. The scanner according to claim 11, additionally comprising a handle (27) on which the cantilevers (22, 23, 24) are mounted.

13. A device for determining the 3D coordinates of an object (3, 4, 5), in particular of a tooth or a plurality of teeth or a dental cast, with a scanner (1) for scanning the object (3, 4, 5) and evaluation means for determining the 3D coordinates of the object (3, 4, 5) from the images taken by the scanner (1), comprising a scanner (1) according to claim 1.

14. The device according to claim 13, comprising a tracking system (26) for determining the location and orientation of the scanner (1).

15. The scanner according to claim 1, wherein the beam splitter (13) additionally comprises first and second mirror surfaces (15,17) each positioned to respectively reflect light reflected from the first and second mirrors (14, 16) to the image sensor (18).

16. The scanner according to claim 1, wherein the projector (2) comprises a light source (6), pattern transparency (7) and projection optics (8) arranged in this order for projecting the pattern (7) onto the object (3, 4, 5).

17. A scanner for scanning an object (3,4,5) with a projector (2) for projecting a pattern (7) onto the object (3,4,5) and with a camera which comprises a recording optics and an image sensor (18), wherein the recording optics comprises a first imaging optics (9) and a second imaging optics (10) and a beam splitter (13) positioned to receive light respectively projected from the first imaging optics (9) and second imaging optics (10) and then reflecting the light to the image sensor (18), markers (27, 28, 29; 30, 31,32; 33) for a tracking system (26) are provided on the scanner (1), and additionally comprising cantilevers (22, 23, 24) on which the markers (27, 28, 29; 30, 31,32; 33) are mounted, and three said cantilevers (22, 23, 24) and seven said markers (27, 28, 29; 30, 31,32, 33), with two cantilevers (22, 23) each having three markers (27, 28, 29; 30, 31, 32) mounted thereon and one cantilever (24) having one sensor (33) mounted thereon.

\* \* \* \* \*